United States Patent
Dube et al.

(10) Patent No.: US 7,348,433 B2
(45) Date of Patent: Mar. 25, 2008

(54) QUINOLINONES AS PROSTAGLANDIN RECEPTOR LIGANDS

(75) Inventors: Daniel Dube, St-Lazare (CA); Denis Deschenes, Dorval (CA); Rejean Fortin, Montreal Nord (CA); Yves Girard, Lille-Bizard (CA)

(73) Assignee: Merck Frosst Canada & Co., Quebec (CA)

( * ) Notice: Subject to any disclaimer, the term of this patent is extended or adjusted under 35 U.S.C. 154(b) by 713 days.

(21) Appl. No.: 10/498,084

(22) PCT Filed: Dec. 11, 2002

(86) PCT No.: PCT/CA02/01914

§ 371 (c)(1),
(2), (4) Date: Jun. 10, 2004

(87) PCT Pub. No.: WO03/051878

PCT Pub. Date: Jun. 26, 2003

(65) Prior Publication Data

US 2005/0222194 A1    Oct. 6, 2005

Related U.S. Application Data

(60) Provisional application No. 60/340,439, filed on Dec. 14, 2001.

(51) Int. Cl.
*C07D 215/00* (2006.01)
*A01N 43/42* (2006.01)
*A61K 31/47* (2006.01)

(52) U.S. Cl. .................. 546/157; 514/309
(58) Field of Classification Search .............. 546/157
See application file for complete search history.

(56) References Cited

U.S. PATENT DOCUMENTS

| 5,378,694 A | 1/1995 | Afonso et al. |
|---|---|---|
| 5,412,104 A | 5/1995 | Afonso et al. |
| 5,942,522 A | 8/1999 | Afonso et al. |
| 6,184,231 B1 | 2/2001 | Hewawasam et al. |
| 6,265,421 B1 | 7/2001 | Pystynen et al. |

FOREIGN PATENT DOCUMENTS

| WO | WO 92/04327 | 3/1992 |
|---|---|---|
| WO | WO 92/04328 | 3/1992 |
| WO | WO 97/37977 | 10/1997 |

OTHER PUBLICATIONS

Stadlbauer, Wolfgag, et al—Organisch Chemie, vol. 37B (9), pp. 1196-1200, 1982.
Laschober, Rita, et al—Liebigs annalen Der Chemie, vol. 11, pp. 1083-1086, 1990.
Kappe, Thomas, et al—Tetrahedron, vol. 51 (47), pp. 12923-12928, 1995.
Chemical Abstracts, vol. 53, Abstract No. 11415e, 1959.
Chemical Abstracts, vol. 57, Abstract No. 12444e, 1962.
Chemical Abstracts, vol. 65, Abstract No. 3845c, 1966.
Chemical Abstracts, vol. 57, Abstract No. 9824e, 1962.
Chemical Abstracts, vol. 57, Abstract No. 12446e, 1962.

*Primary Examiner*—Cecilia J. Tsang
*Assistant Examiner*—Barbara Frazier
(74) *Attorney, Agent, or Firm*—Curtis C. Panzer; Raynard Yuro; Valerie J. Camara

(57) ABSTRACT

This invention encompasses a method for treating a prostaglandin E mediated disease or condition comprising administering to a mammalian patient in need of such treatment a compound of Formula (A) in an amount that is effective to treat the prostaglandin E mediated disease or condition

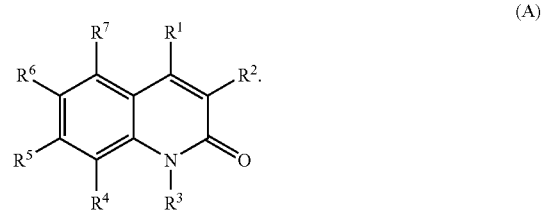

(A)

6 Claims, No Drawings

QUINOLINONES AS PROSTAGLANDIN RECEPTOR LIGANDS

CROSS REFERENCE TO RELATED APPLICATIONS

This application is a U.S. National Phase application under 35 U.S.C. § 371 of PCT Application No. PCT/CA02/01914, filed Dec. 11, 2002, which claims priority under 35 U.S.C. 119 to 60/340,439, filed Dec. 14, 2001.

BACKGROUND OF THE INVENTION

This invention relates to compounds and methods for treating prostaglandin E mediated diseases, and certain pharmaceutical compositions thereof. More particularly, the compounds of the invention are structurally different from NSAIDs and opiates, and are antagonists of the pain and inflammatory effects of E-type prostaglandins.

Two review articles describe the characterization and therapeutic relevance of the prostanoid receptors as well as the most commonly used selective agonists and antagonists: *Eicosanoids From Biotecnology to Therapeutic Applications*, Folco, Samuelsson, Maclouf, and Velo eds, Plenum Press, New York, 1996, chap. 14, 137-154 and Journal of Lipid Mediators and Cell Signalling, 1996, 14, 83-87. An article from *The British Journal of Pharmacology* (1994, 112, 735-740) suggests that Prostaglandin $E_2$ ($PGE_2$) exerts allodynia through the $EP_1$ receptor subtype and hyperalgesia through $EP_2$ and $EP_3$ receptors in the mouse spinal cord.

Thus, selective prostaglandin ligands, agonists or antagonists, depending on which prostaglandin E receptor subtype is being considered, have anti-inflammatory, antipyretic and analgesic properties similar to a conventional non-steroidal anti-inflammatory drug, and in addition, inhibit hormone-induced uterine contractions and have anti-cancer effects. These compounds have a diminished ability to induce some of the mechanism-based side effects of NSAIDs which are indiscriminate cyclooxygenase inhibitors. In particular, the compounds have a reduced potential for gastrointestinal toxicity, a reduced potential for renal side effects, a reduced effect on bleeding times and a lessened ability to induce asthma attacks in aspirin-sensitive asthmatic subjects.

In The American Physiological Society (1994, 267, R289-R-294), studies suggest that PGE2-induced hyperthermia in the rat is mediated predominantly through the EP1 receptor. World patent applications WO 96/06822 (Mar. 7, 1996), WO 96/11902 (Apr. 25, 1996) and EP 752421-A1 (Jan. 08, 1997) disclose compounds as being useful in the treatment of prostaglandin mediated diseases.

SUMMARY OF THE INVENTION

This invention encompasses a method for treating a prostaglandin E mediated disease or condition comprising administering to a mammalian patient in need of such treatment a compound of Formula A:

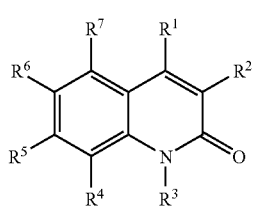

in an amount that is effective to treat the prostaglandin E mediated disease or condition.

DETAILED DESCRIPTION OF THE INVENTION

This invention encompasses a method for treating a prostaglandin E mediated disease or condition comprising administering to a mammalian patient in need of such treatment a compound of Formula A:

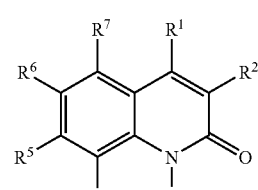

or a pharmaceutically acceptable salt, hydrate, ester or tautomer thereof, wherein:

$R^1$ is selected from the group consisting of:
  (1) hydrogen,
  (2) halo,
  (3) hydroxy,
  (4) $C_{1-6}$alkyl,
  (5) $C_{1-6}$alkenyl,
  (6) $C_{1-6}$alkoxy,
  (7) $C_{1-6}$alkyl-S(O)$_m$—, wherein m is 0, 1, 2 or 3
  (8) $C_{1-6}$alkyl-C(O)—
  (7) $C_{1-6}$alkoxy-C(O)—
  (9) $C_{1-6}$alkyl-C(O)—O—
  (10) aryl,
  (11) aralkyl,
  (12) aryloxy,
  (13) aralkoxy,
  (14) arylthio,
  (15) aroyl,
  (16) aroyloxy, and
  (17) N($R^8$)2,
wherein the alkyl, alkenyl and aryl portions of items (4)-(16) above are optionally substituted from one up to the maximum number of substituable positions with a member independently selected from the group consisting of: halo, heterocycle, $C_{1-6}$alkoxy, $C_{1-6}$alkyl-S(O)$_k$—, wherein k is 0, 1 or 2 $C_{1-6}$alkyl-C(O)—, $C_{1-6}$alkoxy-C(O), $C_{1-6}$alkyl-C(O)—O, carboxy, hydroxy and aralkoxy, the alkyl portions of said $C_{1-6}$alkoxy, $C_{1-6}$alkyl-S(O)$_k$—, $C_{1-6}$alkyl-C(O)—, $C_{1-6}$alkoxy-C(O) and $C_{1-6}$alkyl-C(O)—O groups optionally substituted with 1-3 substituents independently selected from: halo and hydroxy,
said aryl portions of items (10)-(16) above further optionally substituted from one up to the maximum number of substituable positions with $C_{1-6}$alkyl, optionally substituted with 1-3 substituents independently selected from the group consisting of: halo and hydroxy;

$R^2$ is selected from the group consisting of:
  (1) benzyl, optionally substituted with 1-3 substituents independently selected from the group consisting of:
    (a) halo,
    (b) aryl,
    (c) aryloxy,
    (d) aryl-S(O)$_k$—, wherein k is 0, 1 or 2,
    (e) heterocycle,
    (f) aralkyl,
    (g) aroyl,
    (h) aroyloxy, (i) $C_{1-6}$alkyl,
(j) $C_{1-6}$alkenyl,
(k) $C_{1-6}$alkoxy,
(l) $C_{1-6}$alkyl-S(O)$_k$—, wherein k is 0, 1 or 2,
(m) $C_{1-6}$alkyl-C(O)—,
(n) $C_{1-6}$alkoxy-C(O),
(o) $C_{1-6}$alkyl-C(O)—O—,
(p) carboxy,
(q) hydroxy,
(r) N(R8)$_2$,
(s) SO$_2$R$^8$, and
(t) SO$_2$N(R$^8$)$_2$ wherein the alkyl, alkenyl, aryl and heterocycle portions of items (b)-(o) above are optionally substituted from one up to the maximum number of substituable positions with a member independently selected from the group consisting of: halo, heterocycle, $C_{1-6}$alkoxy, $C_{1-6}$alkyl-S(O)$_k$—, wherein k is 0, 1 or 2$C_{1-6}$alkyl-C(O)—, $C_{1-6}$alkoxy-C(O)—, $C_{1-6}$alkyl-C(O)—O—, aralkoxy, carboxy and hydroxy, the alkyl portions of said $C_{1-6}$alkoxy, $C_{1-6}$alkyl-S(O)$_k$—, $C_{1-6}$alkyl-C(O)—, $C_{1-6}$alkoxy-C(O) and $C_{1-6}$alkyl-C(O)—O groups optionally substituted with 1-3 substituents independently selected from halo and hydroxy;

said aryl and heterocycle portions of items (b)-(h) above further optionally substituted from one up to the maximum number of substituable positions with $C_{1-6}$alkyl optionally substituted with 1-3 substituents independently selected from the group consisting of: halo and hydroxy;

(2) $C_{1-7}$alkyl or $C_{1-6}$alkenyl, each optionally substituted with 1-3 groups independently selected from the group consisting of: halo, hydroxy, $C_{3-6}$cycloalkyl, aryl and heterocycle, said aryl and heterocycle optionally substituted with 1-3 substituents independently selected from:

(a) halo,
(b) hydroxy,
(c) aryl, optionally substituted with 1-3 halo groups, and
(d) $C_{1-6}$alkyl, optionally substituted independently with 1-3 halo or hydroxy groups, except that when R$^2$ is methyl monosubstituted with aryl as phenyl then R$^2$ is defined as in (1) above, and (3) aroyl, optionally substituted with aryloxy or arylthio, said aryloxy or arylthio optionally substituted with 1-3 halo groups;

R$^3$ is selected from the group consisting of:

(1) $C_{1-6}$alkyl, $C_{2-6}$alkenyl or $C_{3-6}$alkynyl, each optionally substituted with 1-3 halo groups,
(2) aryl, optionally substituted with 1-3 halo groups, and
(3) aralkyl, optionally substituted with a substituent independently selected from the group consisting of: $C_{1-6}$alkylsulfonyl and halo, R$^4$, R$^5$, R$^6$ and R$^7$ are each independently selected from the group consisting of:

(1) hydrogen,
(2) halo, and
(3) $C_{1-6}$alkyl, optionally substituted with 1-3halo groups, or R3 and R4 may be joined together with the atoms to which they are attached to form a monocyclic ring as shown in Formula A':

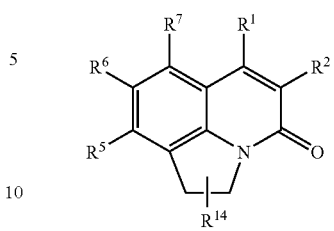

wherein R$^{14}$ is selected from the groups consisting of: halo, $C_{1-6}$alkyl or aryl, wherein $C_{1-6}$alkyl and aryl are optionally substituted with 1-3 halo groups; and R$^8$ is selected from the group consisting of H, $C_{1-6}$alkyl, $C_{1-6}$alkenyl and $C_{1-6}$alkyl-C(O)—, the alkyl and alkenyl portions of which are optionally substituted with 1-3 halo groups, in an amount which is effective for treating the prostaglandin E mediated disease.

For purposes of this Specification, "pharmaceutically acceptable hydrate" means the compounds of the instant invention crystallized with one or more molecules of water to form a hydrated form.

For purposes of this Specification, the term "pharmaceutically acceptable ester" means ester derivative formed at any carboxylic acid of the compounds of the present invention, such as Example 55that may act as a prodrug which, when absorbed into the bloodstream of a warm-blooded animal, may cleave in such a manner as to release the drug form and permit the drug to afford improved therapeutic efficacy.

For purposes of this Specification, "pharmaceutically acceptable tautomer" means any tautomeric form of any compound of the present invention. For example, the compounds of the present invention would include the tautomeric forms shown below:

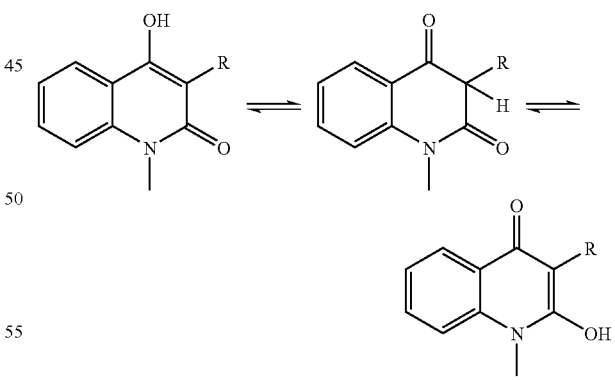

For purposes of this Specification, "treating" a prostaglandin E mediated disease or condition encompasses not only treating a patient with symptoms of the disease or condition but also "prophylactically treating" a patient prior to that patient manifesting symptoms of the disease or condition to prevent said disease or condition. The term "treating" a prostaglandin disease or condition also encompasses preventing the onset or progression of a prostaglandin E mediated disease or condition.

An embodiment of the invention encompasses the above method wherein the prostaglandin E mediated disease or condition is selected from the group consisting of:

(1) pain, fever or inflammation associated with rheumatic fever, influenza or other viral infections, common cold, low back and neck pain, skeletal pain, postpartum pain, dysmenorrhea, headache, migraine, toothache, sprains and strains, myositis, neuralgia, synovitis, arthritis, including rheumatoid arthritis, degenerative joint diseases (osteoarthritis), gout and ankylosing spondylitis, bursitis, burns including radiation and corrosive chemical injuries, sunburns, pain following surgical and dental procedures as well as immune and autoimmune diseases;

(2) cellular neoplastic transformations or metastic tumor growth;

(3) diabetic retinopathy and tumor angiogenesis;

(4) prostanoid-induced smooth muscle contraction associated with dysmenorrhea, premature labor, asthma or eosinophil related disorders;

(5) Alzheimer's disease;

(6) glaucoma;

(7) bone loss;

(8) osteoporosis;

(9) promotion of bone formation;

(10) Paget's disease;

(11) cytoprotection in peptic ulcers, gastritis, regional enteritis, ulcerative colitis, diverticulitis or other gastrointestinal lesions;

(12) GI bleeding and patients undergoing chemotherapy;

(13) coagulation disorders selected from hypoprothrombinemia, haemophilia and other bleeding problems;

(14) kidney disease;

(15) thrombosis;

(16) occlusive vascular disease;

(17) presurgery;

(18) anti-coagulation;

(19) neuropathic pain; and

(20) urinary incontinence.

Another embodiment of the invention encompasses the above method wherein the prostaglandin E mediated disease is selected from the group consisting of: pain, fever or inflammation associated with rheumatic fever, influenza or other viral infections, common cold, low back and neck pain, skeletal pain, post-partum pain, dysmenorrhea, headache, migraine, toothache, sprains and strains, myositis, neuralgia, synovitis, arthritis, including rheumatoid arthritis, degenerative joint diseases (osteoarthritis), gout and ankylosing spondylitis, bursitis, burns including radiation and corrosive chemical injuries, sunburns, pain following surgical and dental procedures as well as immune and autoimmune diseases.

Another embodiment of the invention encompasses the above method wherein the prostaglandin E mediated disease or condition is pain, fever or inflammation associated with dysmenorrhea.

Another embodiment of the invention encompasses the above method for treating a prostaglandin E mediated disease or condition comprising administering to a mammalian patient in need of such treatment a compound of Formula A:

A or a pharmaceutically acceptable salt thereof, said variables as defined above, wherein the compound of Formula A is co-administered with other agents or ingredients.

Within this embodiment is encompassed the method wherein the compound of Formula A is co-administered with another agent or ingredient selected from the group consisting of:

(1) an analgesic selected from acetaminophen, phenacetin, aspirin, a narcotic;

(2) a cyclooxygenase-2 selective nonsteroidal anti-inflammatory drug or a conventional nonsteroidal anti-inflammatory drug;

(3) caffeine;

(4) an $H_2$-antagonist;

(5) aluminum or magnesium hydroxide;

(6) simethicone;

(7) a decongestant selected from phenylephrine, phenylpropanolamine, pseudophedrine, oxymetazoline, ephinephrine, naphazoline, xylometazoline, propylhexedrine, or levodesoxyephedrine;

(8) an antiitussive selected from codeine, hydrocodone, caramiphen, carbetapentane and dextramethorphan;

(9) another prostaglandin ligand selected from misoprostol, enprostil, rioprostil, ornoprostol and rosaprostol; a diuretic; and

(10) a sedating or non-sedating antihistamine. Examples of COX-2 inhibitors are disclosed in U.S. Pat. Nos. 5,474,995; 5,633,272; and 5,466,823; and in WO 96/25405, WO 97/38986, WO 98/03484, WO 97/14691, and WO 95/0051.

Also, within this embodiment is encompassed the method wherein the compound of Formula A is co-administered with a cyclooxygenase-2 selective nonsteroidal anti-inflammatory drug or a conventional nonsteroidal anti-inflammatory drug.

Also within this embodiment is encompassed the method wherein the compound of Formula A is co-administered with a conventional nonsteroidal anti-inflammatory drug selected from the group consisting of: aspirin, ibuprofen, naproxen, and ketoprofen.

Also within this embodiment is encompassed the method wherein the compound is co-administered with a cyclooxygenase-2 selective nonsteroidal anti-inflammatory drug selected from rofecoxib, etoricoxib, valdecoxib, parecoxib and celecoxib.

Another embodiment of the invention encompasses the method for treating a prostaglandin E mediated disease or condition comprising administering to a mammalian patient in need of such treatment a compound of Formula A or a pharmaceutically acceptable salt thereof, wherein $R^2$ is benzyl, optionally substituted with 1-3 substituents independently selected from the group consisting of:

(a) halo, (b) aryl, (c) aryloxy, (d) aryl-S(O)k, wherein k is 0, 1 or 2, (e) heterocycle,
(f) aralkyl,
(g) aroyl,
(h) aroyloxy,
(i) $C_{1-6}$alkyl,
(j) $C_{1-6}$alkenyl,
(k) $C_{1-6}$alkoxy,
(l) $C_{1-6}$alkyl-S(O)$_k$—, wherein k is 0, 1 or 2,
(m) $C_{1-6}$alkyl-C(O)—,
(n) $C_{1-6}$alkoxy-C(O),
(o) $C_{1-6}$alkyl-C(O)—O—,
(p) carboxy,
(q) hydroxy, and
(r) N(R8)2, wherein the alkyl, alkenyl, aryl and heterocycle portions of items (b)-(o) above are optionally substituted from one up to the maximum number of substituable positions with a member independently selected from the group consisting of: halo, heterocycle, $C_{1-6}$alkoxy, $C_{1-6}$alkyl-S(O)$_k$—, $C_{1-6}$alkyl-C(O)—, $C_{1-6}$alkoxy-C(O)—, $C_{1-6}$alkyl-C(O)—O—, aralkoxy, carboxy and hydroxy, the alkyl portions of said $C_{1-6}$alkoxy, $C_{1-6}$alkyl-S(O)$_k$—, $C_{1-6}$alkyl-C(O)—, $C_{1-6}$alkoxy-C(O) and $C_{1-6}$alkyl-C(O)—O groups optionally substituted with 1-3 substituents independently selected from halo and hydroxy;

said aryl and heterocycle portions of items (b)-(h) above further optionally substituted from one up to the maximum number of substituable positions with $C_{1-6}$alkyl optionally substituted with 1-3 substituents independently selected from the group consisting of: halo and hydroxy.

Another embodiment of the invention encompasses the method for treating a prostaglandin E mediated disease or condition comprising administering to a mammalian patient in need of such treatment a compound of Formula A or a pharmaceutically acceptable salt thereof, wherein $R^2$ is mono-, di or tri substituted benzyl, wherein the substituents are independently selected from the group consisting of:
(a) aryl,
(b) aryloxy,
(c) aryl-S(O)$_k$—, wherein k is 0, 1 or 2,
(d) heterocycle,
(e) aralkyl,
(f) aroyl, and
(g) aroyloxy, the aryl and heterocycle portions of items (a)-(g) above are optionally substituted from one up to the maximum number of substituable positions with a member independently selected from the group consisting of: halo, $C_{1-6}$alkyl, $C_{1-6}$alkoxy, $C_{1-6}$alkyl-S(O)$_k$—, $C_{1-6}$alkyl-C(O)—, $C_{1-6}$alkoxy-C(O)—, $C_{1-6}$alkyl-C(O)—O—, aralkoxy, carboxy and hydroxy, the alkyl portions of said $C_{1-6}$alkoxy, $C_{1-6}$alkyl-S(O)$_k$—, $C_{1-6}$alkyl-C(O)—, $C_{1-6}$alkoxy-C(O) and $C_{1-6}$alkyl-C(O)—O groups optionally substituted with 1-3 substituents independently selected from halo and hydroxy.

Another embodiment of the invention encompasses the method for treating a prostaglandin E mediated disease or condition comprising administering to a mammalian patient in need of such treatment a compound of Formula A or a pharmaceutically acceptable salt thereof, wherein $R^2$ is mono-, di- or tri-substituted benzyl, with the proviso that at least one of the substituents is attached to the benzyl group at the 4-position.

Another embodiment of the invention encompasses the method for treating a prostaglandin E mediated disease or condition comprising administering to a mammalian patient in need of such treatment a compound of Formula A or a pharmaceutically acceptable salt thereof, wherein $R^1$ is methoxy, difluoromethoxy, hydroxy or amino.

Another embodiment of the invention encompasses the method for treating a prostaglandin E mediated disease or condition comprising administering to a mammalian patient in need of such treatment a compound of Formula A or a pharmaceutically acceptable salt thereof, wherein R3 is benzyl, phenyl, ethyl, propyl, methyl or allyl.

The present invention also encompasses the method for treating a prostaglandin E mediated disease or condition comprising administering to a mammalian patient in need of such treatment a compound from the following tables:

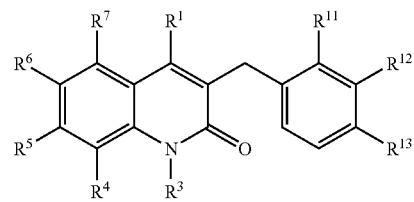

| $R^1$ | $R^3$ | $R^4$ | $R^5$ | $R^6$ | $R^7$ | $R^{11}$ | $R^{12}$ | $R^{13}$ |
|---|---|---|---|---|---|---|---|---|
| OMe | benzyl | H | H | H | H | H | H | H |
| OH | 4-MeSO2benzyl | H | H | H | H | H | H | H |
| OH | benzyl | H | H | H | H | H | H | 4-MeSO2 |
| OH | n-butyl | H | H | H | H | H | H | H |
| Me | benzyl | H | H | H | H | H | H | H |
| OH | iso-propyl | H | H | H | H | H | H | H |
| OH | Me | H | H | H | H | H | H | H |
| OH | phenyl | H | H | H | H | H | H | H |
| OH | Me | H | H | H | H | H | H | Me |
| OH | benzyl | Me | H | H | H | H | H | H |
| OH | ethyl | Me | H | H | H | H | H | H |
| OH | Me | H | Cl | H | H | H | H | phenyl |
| OH | Me | H | H | Cl | H | H | H | 3-Cl-4-F-phenyl |
| NH2 | Me | H | H | H | H | F | H | 3-Cl-4-F-phenyl |
| OH | Me | H | H | H | H | H | H | OMe |
| OH | Me | H | H | H | H | H | H | CO2Me |

-continued

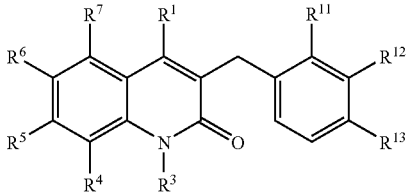

| R$^1$ | R$^3$ | R$^4$ | R$^5$ | R$^6$ | R$^7$ | R$^{11}$ | R$^{12}$ | R$^{13}$ |
|---|---|---|---|---|---|---|---|---|
| OH | Me | H | H | H | H | H | CO2H | H |
| OH | Me | H | H | H | H | H | H | CO2H |
| OH | Me | H | H | H | H | H | H | SMe |
| OH | Me | H | H | H | H | Me | H | H |
| OH | Me | H | H | H | H | H | Me | H |
| OH | Me | H | H | H | H | H | H | OPh |
| OH | Me | H | H | H | H | H | H | Ph |
| OH | Me | H | H | H | H | H | H | CF3 |
| OH | Me | H | H | H | H | H | H | F |
| OH | Me | H | H | H | H | H | H | NMe2 |
| OH | Me | H | H | H | H | H | H | isopropyl |
| OH | ethyl | H | H | H | H | H | H | Me |
| OH | Me | H | H | H | H | H | H | 3,4-(OCF2H) |
| OH | Me | H | H | H | H | H | H | phenylsulfonyl |
| OH | Me | H | H | H | H | H | H | 4-Cl-thiophenoxy |
| OH | Me | H | H | H | H | H | H | benzoyl |
| OH | Me | H | H | H | H | H | H | bromo |
| OH | Me | H | H | H | H | H | H | 3-Cl-4-F-phenyl |
| OCF2H | Me | H | H | H | H | H | H | phenyl |
| OH | Me | H | H | H | H | H | H | 5-(2-Et-pyridinyl) |
| OH | Me | H | H | H | H | 5-(2-Et-pyridinyl) | H | |
| OH | Me | H | H | H | H | H | 4-CF3-phenyl | H |
| OH | Me | H | H | H | H | H | H | 4-CF3-phenyl |
| OH | Me | H | H | H | H | H | H | 4-tert-butylphenyl |
| OH | Me | H | H | H | H | H | H | 4-acetylphenyl |
| OH | Me | H | H | H | H | H | 4-acetylphenyl | H |
| OH | Me | H | H | H | H | H | H | 4-carboxyphenyl |
| OH | Me | H | H | H | H | H | H | 4-Et-phenyl |
| OMs | Me | H | H | H | H | H | bromo | H |
| OH | Me | H | H | H | H | H | H | phenyl |
| OH | Me | H | H | H | H | H | phenyl | H |
| OH | Me | H | H | H | H | H | 4-carboxyphenyl | H |
| OH | Me | H | H | H | H | H | 4-Cl-phenyl | H |
| OH | Me | H | H | H | H | H | 3-thienyl | H |
| OH | Me | H | H | H | H | H | 4-OCF3-phenyl | H |
| OH | Me | H | H | H | H | H | H | 3-thienyl |
| OH | Me | H | H | H | H | H | H | 2-thienyl |
| OH | Me | H | H | H | H | H | H | 2-naphthyl |
| OH | Me | H | H | H | H | H | H | 4-Cl-phenyl |
| OH | Me | H | H | H | H | H | H | 4-OCF3-phenyl |
| OH | Me | H | H | H | H | H | H | 2-benzothiophene |
| OH | Me | H | H | H | H | H | H | 4-F-phenyl |
| OH | Me | H | H | H | H | H | 2-F-phenyl | H |
| OH | Me | H | H | H | H | H | H | 4-Me-phenyl |
| OH | Me | H | H | H | H | H | H | 4-benzyloxyphenyl |
| OH | Me | H | H | H | H | H | H | α-OH-a-Me-benzyl |
| OH | Me | H | H | H | H | H | H | 1-naphthyl |
| OH | Me | H | H | H | H | H | H | 2-F-phenyl |
| OH | Me | H | H | H | H | H | H | 3-F-phenyl |
| OH | Me | H | H | H | H | H | H | 3-Cl-phenyl |
| OH | Me | H | H | H | H | H | 3-Cl-phenyl | H |
| OH | Me | H | H | H | H | H | 3-F-phenyl | H |
| OH | Me | H | H | H | H | H | H | 4-Cl-phenylsulfonyl |
| OH | Me | H | H | H | H | H | H | α-OH-a-Me-4-Cl-benzyl |
| OH | ethyl | H | H | H | H | H | H | 3-Cl-4-F-phenyl |
| OH | allyl | H | H | H | H | H | H | 3-Cl-4-F-phenyl |
| OH | n-propyl | H | H | H | H | H | H | 3-Cl-4-F-phenyl |
| OH | Me | H | H | H | H | H | H | 4-MeSO2 |
| OH | Me | H | H | H | H | H | 2-benzothiophene | H |
| OH | 4-Cl-benzyl | H | H | H | H | H | H | 3-Cl-4-F-phenyl |
| NH2 | Me | H | H | H | H | H | H | 3-Cl-4-F-phenyl |
| 2-(2-pyridinyl)ethoxy | Me | H | H | H | H | H | H | 3-Cl-4-F-phenyl |
| carbethoxymethoxy | Me | H | H | H | H | H | H | 3-Cl-4-F-phenyl |
| n-butoxy | Me | H | H | H | H | H | H | 3-Cl-4-F-phenyl |
| 2-(Methio)methoxy | Me | H | H | H | H | H | H | 3-Cl-4-F-phenyl |

-continued

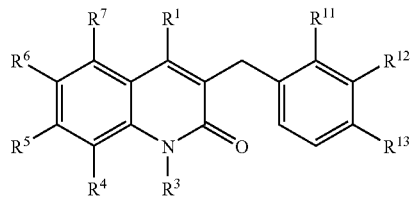

| R$^1$ | R$^3$ | R$^4$ | R$^5$ | R$^6$ | R$^7$ | R$^{11}$ | R$^{12}$ | R$^{13}$ |
|---|---|---|---|---|---|---|---|---|
| O-(3,4-F-benzoyl) | Me | H | H | H | H | H | H | 3-Cl-4-F-phenyl |
| OAc | Me | H | H | H | H | H | H | 3-Cl-4-F-phenyl |
| Cl | Me | H | H | H | H | H | H | 3-Cl-4-F-phenyl |
| OCF2H | Me | H | H | H | H | H | H | phenylsulfonyl |
| OMs | Me | H | H | H | H | H | H | 3-Cl-4-F-phenyl |
| carboxymethoxy | Me | H | H | H | H | H | H | 3-Cl-4-F-phenyl |
| OCF2H | Me | H | H | H | H | H | H | bromo |
| OCF2H | Me | H | H | H | H | H | Bromo | H |
| OH | Me | H | H | H | H | H | H | dimethylcarbinol |
| OCF2H | Me | H | H | H | H | H | H | 4-Me-phenyl |
| OCF2H | Me | H | H | H | H | H | H | 3-Me-phenyl |
| OCF2H | Me | H | H | H | H | H | 4-Me-phenyl | H |
| OCF2H | Me | H | H | H | H | H | 3-Me-phenyl | H |
| NH2 | Me | H | H | H | H | H | H | Me |
| OH | Me | H | H | H | H | H | H | CO2Et |
| OCF2H | allyl | H | H | H | H | H | H | 3-Cl-4-F-phenyl |
| OH | 2-Me-2-propene | H | H | H | H | H | H | 3-Cl-4-F-phenyl |
| OH | Me | H | H | H | H | H | Dimethylcarbinol | H |
| OH | propargyl | H | H | H | H | H | H | 3-Cl-4-F-phenyl |
| OH | 2-bromo-2-propene | H | H | H | H | H | H | 3-Cl-4-F |
| OH | allyl | H | H | H | H | H | H | 4-Cl-thiophenoxy |
| OCF2H | allyl | H | H | H | H | H | H | 4-Cl-thiophenoxy |
| Me2N | Me | H | H | H | H | H | H | Me |
| NHAc | Me | H | H | H | H | H | H | Me |
| NH2 | allyl | H | H | H | H | H | H | 4-Cl-thiophenoxy |
| NHallyl | allyl | H | H | H | H | H | H | 4-Cl-thiophenoxy |
| NH2 | Me | H | H | H | H | H | H | bromo |
| 2-hydroxyethoxy | Me | H | H | H | H | H | H | 3-Cl-4-F-phenyl |
| NH2 | 2,2,2-trifluoroethyl | H | H | H | H | H | H | 3-Cl-4-F-phenyl |
| NH2 | Me | H | H | H | H | H | H | phenyl |
| NH2 | Me | H | H | H | H | H | H | 4-MeS-phenyl |
| NH2 | Me | H | H | H | H | H | H | 4-MeSO2-phenyl |
| NH2 | allyl | H | H | H | H | H | H | 3-Cl-4-F-phenyl |
| NH2 | allyl | H | H | H | H | H | H | 4-MeSO-phenyl |
| NH2 | allyl | H | H | H | H | H | H | 4-MeSO2-phenyl |
| NH2 | Me | H | H | H | H | H | H | 4-dimethylcarbinolphenyl |

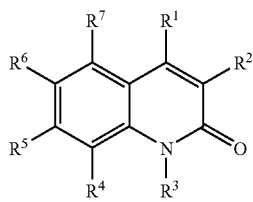

R$^4$ = H; R$^5$ = H, R$^6$ = H; R$^7$ = H

| R$^1$ | R$^2$ | R$^3$ |
|---|---|---|
| OH | Me | benzyl |
| OH | n-butyl | benzyl |
| OH | tert-butyl | benzyl |
| OH | phenetyl | benzyl |
| OH | isobutyl | benzyl |
| OH | α-methylbenzyl | benzyl |
| OH | benzoyl | benzyl |
| OMe | benzoyl | benzyl |
| OH | α-hydroxybenzyl | benzyl |
| OH | cyclohexylmethyl | methyl |
| OH | naphthylmethyl | methyl |

-continued

R$^4$ = H; R$^5$ = H, R$^6$ = H; R$^7$ = H

| R$^1$ | R$^2$ | R$^3$ |
|---|---|---|
| OH | n-heptyl | methyl |
| OH | n-butyl | methyl |
| OH | 3-phenyl-2-propenyl | methyl |
| OH | 3-phenyl-propyl | methyl |
| OH | phenethyl | methyl |
| OH | 1-naphthylmethyl | methyl |
| OH | 4-(Cl-thiophenoxy)benzoyl | methyl |
| NH2 | 2-(3-Cl-4-F-phenyl)-5-picolyl | methyl |

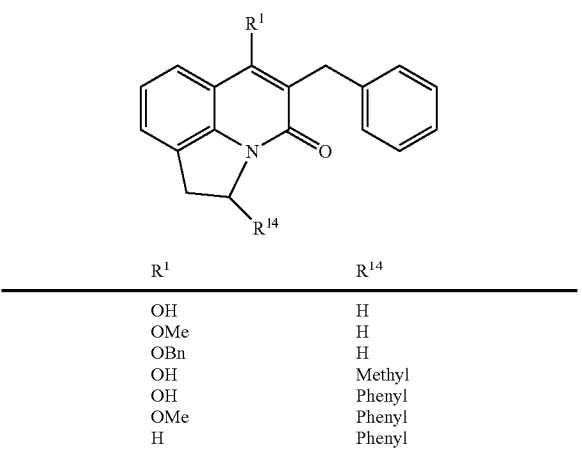

| R¹   | R¹⁴    |
|------|--------|
| OH   | H      |
| OMe  | H      |
| OBn  | H      |
| OH   | Methyl |
| OH   | Phenyl |
| OMe  | Phenyl |
| H    | Phenyl |

Another embodiment of the invention encompasses a compound of Formula B

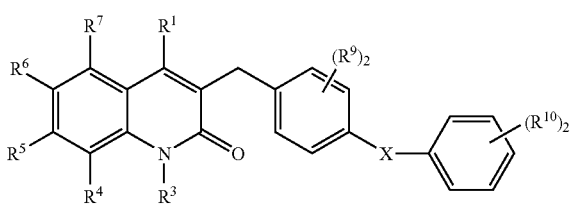

B or a pharmaceutically acceptable salt, hydrate, ester or tautomer thereof, wherein:

X is selected from a bond, O or S(O)k, wherein k is 0, 1 or 2, $R^1$ is selected from the group consisting of:
 (1) hydrogen,
 (2) halo,
 (3) hydroxy,
 (4) $C_{1-6}$alkyl,
 (5) $C_{1-6}$alkenyl,
 (6) $C_{1-6}$alkoxy,
 (7) $C_{1-6}$alkyl-S(O)$_m$—, wherein m is 0, 1, 2 or 3
 (8) $C_{1-6}$alkyl-C(O)—
 (7) $C_{1-6}$alkoxy-C(O)—
 (9) $C_{1-6}$alkyl-C(O)—O—
 (10) aryl,
 (11) aralkyl,
 (12) aryloxy,
 (13) aralkoxy,
 (14) arylthio,
 (15) aroyl,
 (16) aroyloxy and
 (17) N(R8)2, wherein the alkyl, alkenyl and aryl portions of items (4)-(16) above are optionally substituted from one up to the maximum number of substituable positions with a member independently selected from the group consisting of: halo, heterocycle, $C_{1-6}$alkoxy, $C_{1-6}$alkyl-S(O)$_k$—, $C_{1-6}$alkyl-C(O)—, C1-6alkoxy-C(O), $C_{1-6}$alkyl-C(O)—O, carboxy, hydroxy and aralkoxy, the alkyl portions of said $C_{1-6}$alkoxy, $C_{1-6}$alkyl-S(O)$_k$—, $C_{1-6}$alkyl-C(O)—, $C_{1-6}$alkoxy-C(O) and $C_{1-6}$alkyl-C(O)—O groups optionally substituted with 1-3 substituents independently selected from: halo and hydroxy, said aryl portions of items (10)-(16) above further optionally substituted from one up to the maximum number of substituable positions with $C_{1-6}$alkyl, optionally substituted with 1-3 substituents independently selected from the group consisting of: halo and hydroxy;

$R^3$ is selected from the group consisting of:
 (1) $C_{1-6}$alkyl, $C_{2-6}$alkenyl or $C_{3-6}$alkynyl, each optionally substituted with 1-3 halo groups.
 (2) aryl, optionally substituted with 1-3 halo groups,
 (3) aralkyl, optionally substituted with a substituent independently selected from the group consisting of: $C_{1-6}$alkylsulfonyl and halo, $R^4$, $R^5$, $R^6$ and $R^7$ are each independently selected from the group consisting of:
 (1) hydrogen,
 (2) halo, and
 (3) $C_{1-6}$alkyl, optionally substituted with 1-3 halo groups,
or R3 and R4 may be joined together with the atoms to which they are attached to form a monocyclic ring as shown in Formula B':

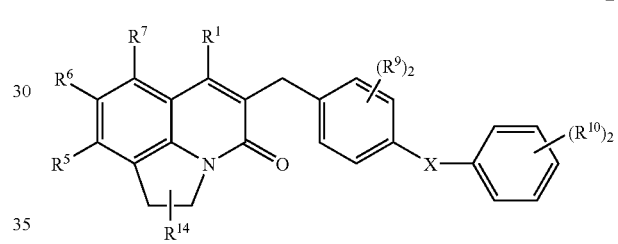

B' wherein $R^{14}$ is selected from the groups consisting of: halo, $C_{1-6}$alkyl, aryl or heterocycle, wherein $C_{1-6}$alkyl, heterocycle and aryl are optionally substituted with 1-3 substituents independently selected from halo, $C_{1-3}$alkyl, carboxy, $SO_2C_{1-3}$alkyl or $SO_2N(C_{1-3}$alkyl$)_2$ said $C_{1-3}$alkyl is optionally substituted with a hydroxy group, and $R^8$ is selected from the group consisting of H, $C_{1-6}$allyl, $C_{1-6}$alkenyl, $C_{1-6}$alkyl-C(O)— and aryl, the aryl, alkyl and alkenyl portions are optionally substituted with 1-3 halo groups, $R_9$ and $R_{10}$ are independently selected from the group consisting of:
 (1) halo,
 (2) $C_{1-6}$alkyl,
 (3) $C_{1-6}$alkenyl,
 (4) $C_{1-6}$alkoxy,
 (5) $C_{1-6}$alkyl-S(O)$_k$—, wherein k is 0, 1 or 2,
 (6) $C_{1-6}$alkyl-C(O)—,
 (7) $C_{1-6}$alkoxy-C(O),
 (8) $C_{1-6}$alkyl-C(O)—O—,
 (9) carboxy,
 (10) hydroxy, and
 (11) N(R8)2, wherein the alkyl and alkenyl portions of items (2)-(8) above are optionally substituted from one up to the maximum number of substituable positions with a member independently selected from the group consisting of: halo, heterocycle, $C_{1-6}$alkoxy, $C_{1-6}$alkyl-S(O)$_k$—, $C_{1-6}$alkyl-C(O)—, $C_{1-6}$alkoxy-C(O)—, $C_{1-6}$alkyl-C(O)—O—, aralkoxy, carboxy and hydroxy, the alkyl portions of said $C_{1-6}$alkoxy, $C_{1-6}$alkyl-S(O)$_k$—, $C_{1-6}$alkyl-C(O)—, $C_{1-6}$alkoxy-C(O) and $C_{1-6}$alkyl-C(O)—O groups optionally substituted with 1-3 substituents independently selected from halo and hydroxy.

Within this embodiment is encompassed the compound of Formula B wherein:

X is selected from a bond, O or S(O)k, wherein k is 0, 1 or 2, $R^1$ is selected from the group consisting of:
(1) halo,
(2) hydroxy,
(3) $C_{1-6}$alkyl,
(4) $C_{1-6}$alkoxy, and
(5) $N(R^8)_2$, wherein $R^8$ is H or $C_{1-4}$alkyl, wherein the alkyl portions of items (3)-(4) above are optionally substituted with 1-3 halo groups, $R^3$ is $C_{1-6}$alkyl or C2-4alkenyl, each optionally substituted with 1-3 halo groups.

$R^4$, $R^5$, $R^6$, $R^7$ and $R_9$ are each H, and $R_{10}$ is H or halo.

The present invention also encompasses a compound selected from the group consisting of:
(1) 3-{4-[(4-chlorophenyl)thio]benzyl}-4-hydroxy-1-methylquinolin-2(1H)-one;
(2) 1-allyl-3-{4-[(4-chlorophenyl)thio]benzyl}-4-hydroxyquinolin-2(1H)-one;
(3) 1-allyl-4-amino-3-{4-[(4-chlorophenyl)thio]benzyl}quinolin-2(1H)-one;
(4) 3-[(3'-chloro-4'-fluoro-1,1'-biphenyl4-yl)methyl]-4-hydroxy-1-methylquinolin-2(1H)-one;
(5) 1-allyl-3-[(3'-chloro-4'-fluoro-1,1'-biphenyl-4-yl)methyl]-4-hydroxyquinolin-2(1H)-one;
(6) 4-amino-3-[(3'-chloro-4'-fluoro-1,1'-biphenyl-4-yl)methyl]-1-methylquinolin-2(1H)-one;
(7) 3-[(3'-chloro-4'-fluoro-1,1'-biphenyl-4-yl)methyl]-4-(difluoromethoxy)-1-methylquinolin-2(1H)-one; and
(8) 3-{4-[(4-chlorophenyl)sulfonyl]benzyl}-4-hydroxy-1-methylquinolin-2(1H)-one.

Another embodiment of the invention encompasses a pharmaceutical composition comprising a compound of Formula B in combination with a pharmaceutically acceptable carrier.

The invention is described using the following definitions unless otherwise indicated.

The term "halogen" or "halo" includes F, Cl, Br, and I.

The term "alkyl" means linear or branched structures and combinations thereof, having the indicated number of carbon atoms. Thus, for example, $C_{1-6}$alkyl includes methyl, ethyl, propyl, 2-propyl, s- and t-butyl, butyl, pentyl, hexyl, 1,1-dimethylethyl, cyclopropyl, cyclobutyl, cyclopentyl and cyclohexyl.

The term "alkoxy" means alkoxy groups of a straight, branched or cyclic configuration having the indicated number of carbon atoms. $C_{1-6}$alkoxy, for example, includes methoxy, ethoxy, propoxy, isopropoxy, and the like.

The term "alkylthio" means alkylthio groups having the indicated number of carbon atoms of a straight, branched or cyclic configuration. $C_{1-6}$alkylthio, for example, includes methylthio, propylthio, isopropylthio, and the like.

The term "alkenyl" means linear or branched structures and combinations thereof, of the indicated number of carbon atoms, having at least one carbon-to-carbon double bond, wherein hydrogen may be replaced by an additional carbon-to-carbon double bond. $C_{2-6}$alkenyl, for example, includes ethenyl, propenyl, 1-methylethenyl, butenyl and the like.

The term "alkynyl" means linear or branched structures and combinations thereof, of the indicated number of carbon atoms, having at least one carbon-to-carbon triple bond. $C_{3-6}$alkynyl, for example, includes , propenyl, 1-methylethenyl, butenyl and the like.

The term "cycloalkyl" means mono-, bi- or tri-cyclic structures, optionally combined with linear or branched structures, the indicated number of carbon atoms. Examples of cycloalkyl groups include cyclopropyl, cyclopentyl, cycloheptyl, adamantyl, cyclododecylmethyl, 2-ethyl-1-bicyclo[4.4.0]decyl, and the like.

The term "aryl" is defined as a mono- or bi-cyclic aromatic ring system and includes, for example, phenyl, naphthyl, and the like.

The term "aralkyl" means an alkyl group as defined above of 1 to 6 carbon atoms with an aryl group as defined above substituted for one of the alkyl hydrogen atoms, for example, benzyl and the like.

The term "aryloxy" means an aryl group as defined above attached to a molecule by an oxygen atom (aryl-O) and includes, for example, phenoxy, naphthoxy and the like.

The term "aralkoxy" means an aralkyl group as defined above attached to a molecule by an oxygen atom (aralkyl-O) and includes, for example, benzyloxy, and the like.

The term "arylthio" is defined as an aryl group as defined above attached to a molecule by an sulfur atom (aryl-S) and includes, for example, thiophenyoxy, thionaphthoxy and the like.

The term "aroyl" means an aryl group as defined above attached to a molecule by an carbonyl group (aryl-C(O)—) and includes, for example, benzoyl, naphthoyl and the like.

The term "aroyloxy" means an aroyl group as defined above attached to a molecule by an oxygen atom (aroyl-O) and includes, for example, benzoyloxy or benzoxy, naphthoyloxy and the like.

The term "heterocycle" is defined as a 5- to 10-membered aromatic, partially aromatic or non-aromatic mono- or bicyclic ring, containing 1-3 heteroatoms selected from O, S and N, and optionally substituted with 1-2 oxo groups. Preferably, "heterocycle" is a 5- or 6-membered aromatic or non-aromatic monocyclic ring containing 1-3 heteroatoms selected from O, S and N, for example, pyridine, pyrimidine, pyridazine, furan, thiophene, thiazole, oxazole, isooxazole and the like, or heterocycle is a 9- or 10-membered aromatic or partially aromatic bicyclic ring containing 1-3 heteroatoms selected from O, S, and N, for example, benzofuran, benzothiophene, indole, pyranopyrrole, benzopyran, quionoline, benzocyclohexyl, naphtyridine and the like. "Heterocycle" also includes the following: benzimidazolyl, benzofuranyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthyridinyl, oxadiazolyl, oxazolyl, pyrazinyl, pyrazolyl, pyridopyridinyl, pyridazinyl, pyridyl, pyrimidyl, pyrrolyl, quinazolinyl, quinolyl, quinoxalinyl, thiadiazolyl, thiazolyl, thienyl, triazolyl, azetidinyl, 1,4-dioxanyl, hexahydroazepinyl, piperazinyl, piperidinyl, pyrrolidinyl, morpholinyl, thiomorpholinyl, dihydrobenzimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl.

For purposes of this specification, the following abbreviations have the indicated meanings:

BOC=t-butyloxycarbonyl
Bn=benzyl
CBZ=carbobenzoxy
DCC=1,3-dicyclohexylcarbodiimide
DCM=dichloromethane
DIBAL=diisobutyl aluminum hydride
DIEA=N,N-diisoproylethylamine
DMAP=4-(dimethylamino)pyridine
EDCI=1-(3-dimethylaminopropyl)-3-ethylcarbodiimide hydrochloride
EDTA=ethylenediaminetetraacetic acid, tetrasodium salt hydrate
FAB=fast atom bombardment
FMOC=9-fluorenylmethoxycarbonyl
HMPA=hexamethylphosphoramide
HATU=O-(7-Azabenzotriazol-1-yl)N,N,N',N'-tetramethyluronium hexafluorophosphate
HOBt=1-hydroxybenzotriazole
HRMS=high resolution mass spectrometry
ICBF=isobutyl chloroformate
KHMDS=potassium hexamethyldisilazane
LDA=lithium diisopropylamide
MCPBA=metachloroperbenzoic acid
Ms=methanesulfonyl=mesyl
MsO=methanefulfonate=mesylate
NBS=N-bromosuccinimide
NMM=4-methylmorpholine
PCC=pyridinium chlorochromate
PDC=pyridinium dichromate
Ph=phenyl
PPTS=pyridinium p-toluene sulfonate
pTSA=p-toluene sulfonic acid
r.t.=room temperature
rac.=racemic
TfO=trifluoromethanesulfonate=triflate
THF=tetrahydrofuran
TLC=thin layer chromatography Alkyl group abbreviations
Me=methyl
Et=ethyl
n-Pr=normal propyl
i-Pr=isopropyl
n-Bu=normal butyl
i-Bu=isobutyl
s-Bu=secondary butyl
t-Bu=tertiary butyl Salts The pharmaceutical compositions of the present invention comprise a compound of Formula A or B as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that in the discussion of methods of treatment which follows, references to the compounds of Formula A or B are meant to also include the pharmaceutically acceptable salts.

Dose Ranges

The magnitude of prophylactic or therapeutic dose of a compound of Formula A or B will, of course, vary with the nature and the severity of the condition to be treated and with the particular compound of Formula A and its route of administration. It will also vary according to a variety of factors including the age, weight, general health, sex, diet, time of administration, rate of excretion, drug combination and response of the individual patient. In general, the daily dose from about 0.001 mg to about 100 mg per kg body weight of a mammal, preferably 0.01 mg to about 10 mg per kg. On the other hand, it may be necessary to use dosages outside these limits in some cases.

The amount of active ingredient that may be combined with the carrier materials to produce a single dosage form will vary depending upon the host treated and the particular mode of administration. For example, a formulation intended for the oral administration of humans may contain from 0.5 mg to 5 g of active agent compounded with an appropriate and convenient amount of carrier material which may vary from about 5 to about 95 percent of the total composition. Dosage unit forms will generally contain between from about 1 mg to about 2 g of an active ingredient, typically 25 mg, 50 mg, 100 mg, 200 mg, 300 mg, 400 mg, 500 mg, 600 mg, 800 mg, or 1000 mg.

Pharmaceutical Compositions

For the treatment of any of the prostanoid mediated diseases compounds of Formula A or B may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, cattle, sheep, dogs, cats, etc., the compound of the invention is effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavouring agents, colouring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water-miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropyl methylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more colouring agents, one or more flavouring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavouring and colouring agents, may also be present.

The pharmaceutical compositions of the invention may also be in the form of an oil-in-water emulsion. The oily phase may be a vegetable oil, for example olive oil or arachis oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavouring and colouring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. Cosolvents such as ethanol, propylene glycol or polyethylene glycols may also be used. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of Formula A or B may also be administered in the form of suppositories for rectal administration of the drug. These compositions can be prepared by mixing the drug with a suitable non-irritating excipient which is solid at ambient temperatures but liquid at the rectal temperature and will therefore melt in the rectum to release the drug. Such materials are cocoa butter and polyethylene glycols.

For topical use, creams, ointments, gels, solutions or suspensions, etc., containing the compound of Formula A or B are employed. (For purposes of this application, topical application shall include mouth washes and gargles.) Topical formulations may generally be comprised of a pharmaceutical carrier, cosolvent, emulsifier, penetration enhancer, preservative system, and emollient.

Utilities

The ability of the compounds of Formula A or B to interact with prostaglandin receptors makes them useful for preventing or reversing undesirable symptoms caused by prostaglandins in a mammalian, especially human subject. This mimicking or antagonism of the actions of prostaglandins indicates that the compounds and pharmaceutical compositions thereof are useful to treat, prevent, or ameliorate in mammals and especially in humans: Pain, fever and inflammation of a variety of conditions including rheumatic fever, symptoms associated with influenza or other viral infections, common cold, low back and neck pain, skeletal pain, post-partum pain, dysmenorrhea, headache, migraine, toothache, sprains and strains, myositis, neuralgia, synovitis, arthritis, including rheumatoid arthritis, degenerative joint diseases (osteoarthritis), gout and ankylosing spondylitis, bursitis, burns including radiation and corrosive chemical injuries, sunburns, pain following surgical and dental procedures as well as immune and autoimmune diseases. In addition, such a compound may inhibit cellular neoplastic transformations and metastic tumor growth and hence can be used in the treatment of cancer. Compounds of formula A may also be of use in the treatment and/or prevention prostaglandin E mediated proliferation disorders such as may occur in diabetic retinopathy and tumor angiogenesis. Compounds of Formula A or B will also inhibit prostanoid-induced smooth muscle contraction by antagonizing contractile prostanoids or mimicking relaxing prostanoids and hence may be use in the treatment of dysmenorrhea, premature labor, asthma and eosinophil related disorders. It will also be of use in the treatment of Alzheimer's disease, the treatment of glaucoma, for the prevention of bone loss (treatment of osteoporosis) and for the promotion of bone formation (treatment of fractures) and other bone diseases such as Paget's disease.

The compounds of the present invention are also useful for treating neuropathic pain and urinary incontinence.

By virtue of its prostanoid or prostanoid antagonist activity, a compound of Formula A or B will prove useful as an alternative to conventional non-steroidal anti-inflammatory drugs (NSAID'S) particularly where such non-steroidal anti-inflammatory drugs may be contraindicated such as in patients with peptic ulcers, gastritis, regional enteritis, ulcerative colitis, diverticulitis or with a recurrent history of gastrointestinal lesions; GI bleeding, coagulation disorders including anemia such as hypoprothrombinernia, haemophilia or other bleeding problems; kidney disease; thrombosis, occlusive vascular diseases; those prior to surgery or taking anti-coagulants. Compounds of Formula A or B will also be useful as a cytoprotective agent for patients under chemotherapy.

Combinations with Other Drugs

Compounds of Formula A or B will be useful as a partial or complete substitute for conventional antiinflammatory or analgesic compounds in preparations wherein they are presently co-administered with other agents or ingredients. Thus in further aspects, the invention encompasses pharmaceutical compositions for treating prostaglandin E2 mediated diseases as defined above comprising a non-toxic therapeutically effective amount of the compound of Formula A or B as defined above and one or more ingredients such as another pain reliever including acetaminophen or phenacetin; a COX-2 selective inhibiting agent; a conventional NSAID; a potentiator including caffeine; an H2-antagonist, aluminum or magnesium hydroxide, simethicone, a decongestant including phenylephrine, phenylpropanolamine, pseudophedrine, oxymetazoline, ephinephrine, naphazoline, xylometazoline, propylhexedrine, or levo-desoxyephedrine; an antiitussive including codeine, hydrocodone, caramiphen, carbetapentane, or dextramethorphan; another prostaglandin ligand including misoprostol, enprostil, rioprostil, ornoprostol or rosaprostol; a diuretic; a sedating or non-sedating antihistamine. In addition, the invention encompasses a method of treating prostaglandin E2 mediated diseases comprising: administration to a patient in need of such treatment a non-toxic therapeutically effective amount of the compound of Formula A, optionally co-administered with one or more of such ingredients as listed immediately above.

METHODS OF SYNTHESIS

Compounds of the present invention can be prepared according to the following methods.

Compounds of the present invention can be prepared according to the methods described in patent WO 92/04327, published Mar. 19, 1992, U.S. Pat. No. 5,942,522, granted Aug. 24, 1999, U.S. Pat. No. 5,412,104, granted May 2, 1995, U.S. Pat. No. 5,378,694, granted Jan. 3, 1995, all of which are hereby incorporated by reference in their entirety, or by the following methods:

Method A

The examples may be prepared by reductive alkylation at C3 of the commercially available N-methyl-4-hydroxy-2-quinolinone with various aldehydes

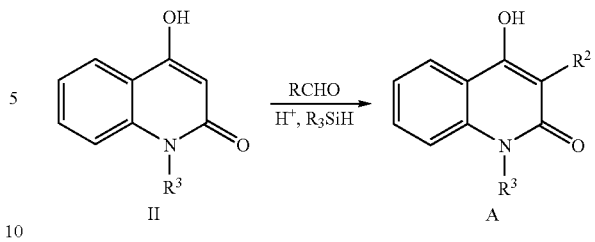

using an acid such as TFA or formic acid with a reducing agent such as Et3SiH in a solvent such as toluene, acetonitrile or formic acid.

Method B

Compound of formula m (for example alkyl anthranilate or anthranilonitrile) can be used to make amino or hydroxyquinolinone by sequential alkylation of amino group with alkylating agents such as acid chloride and alkyl halide using standard protocols. Cyclization to the quinolinone can be performed with a base such as potassium tert-butoxide in a solvent such as THF.

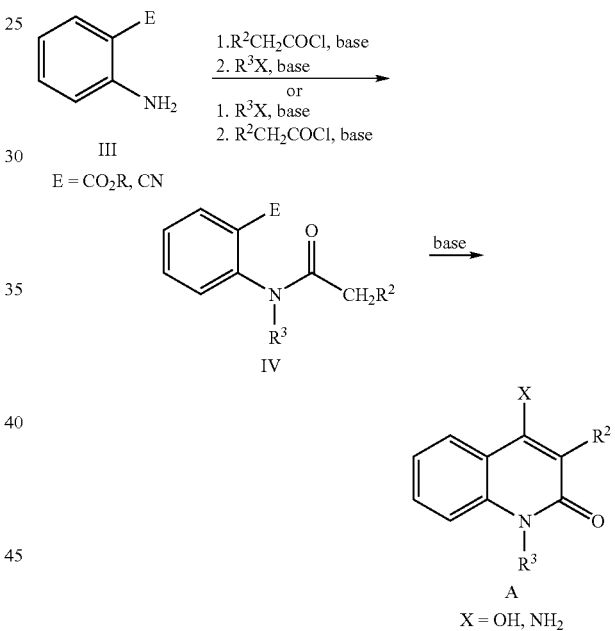

Method C

Compound of formula A' may be prepared by reacting indoline (from commercial sources of via reduction of corresponding indoles (see for ex. B. F. Bowden et al, Aust. J. Chem., 1975, 28, 65-80) with malonates (see T. Kappe, C. O. Kappe, J. Heterocyclic Chem., 1989, 26, 1555).

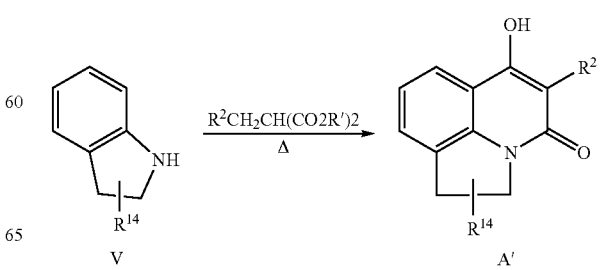

REPRESENTATIVE COMPOUNDS

Table 1 illustrates compounds which are representative of the present invention.

TABLE 1

| Example | R$^1$ | R$^3$ | R$^4$ | R$^5$ | R$^6$ | R$^7$ | R$^{11}$ | R$^{12}$ | R$^{13}$ |
|---|---|---|---|---|---|---|---|---|---|
| 1 | OMe | benzyl | H | H | H | H | H | H | H |
| 2 | OH | 4-MeSO2benzyl | H | H | H | H | H | H | H |
| 3 | OH | benzyl | H | H | H | H | H | H | 4-MeSO2 |
| 4 | OH | n-butyl | H | H | H | H | H | H | H |
| 5 | Me | benzyl | H | H | H | H | H | H | H |
| 6 | OH | iso-propyl | H | H | H | H | H | H | H |
| 7 | OH | Me | H | H | H | H | H | H | H |
| 8 | OH | phenyl | H | H | H | H | H | H | H |
| 16 | OH | Me | H | H | H | H | H | H | Me |
| 17 | OH | benzyl | Me | H | H | H | H | H | H |
| 18 | OH | ethyl | Me | H | H | H | H | H | H |
| 19 | OH | Me | H | Cl | H | H | H | H | phenyl |
| 20 | OH | Me | H | H | Cl | H | H | H | 3-Cl-4-F-phenyl |
| 21 | NH2 | Me | H | H | H | F | H | H | 3-Cl-4-F-phenyl |
| 22 | OH | Me | H | H | H | H | H | H | OMe |
| 23 | OH | Me | H | H | H | H | H | H | CO2Me |
| 24 | OH | Me | H | H | H | H | H | CO2H | H |
| 25 | OH | Me | H | H | H | H | H | H | CO2H |
| 26 | OH | Me | H | H | H | H | H | H | SMe |
| 27 | OH | Me | H | H | H | H | Me | H | H |
| 28 | OH | Me | H | H | H | H | H | Me | H |
| 29 | OH | Me | H | H | H | H | H | H | OPh |
| 30 | OH | Me | H | H | H | H | H | H | Ph |
| 31 | OH | Me | H | H | H | H | H | H | CF3 |
| 32 | OH | Me | H | H | H | H | H | H | F |
| 33 | OH | Me | H | H | H | H | H | H | NMe2 |
| 34 | OH | Me | H | H | H | H | H | H | isopropyl |
| 35 | OH | ethyl | H | H | H | H | H | H | Me |
| 36 | OH | Me | H | H | H | H | H | H | 3,4-(OCF2H) |
| 37 | OH | Me | H | H | H | H | H | H | phenylsulfonyl |
| 38 | OH | Me | H | H | H | H | H | H | 4-Cl-thiophenoxy |
| 39 | OH | Me | H | H | H | H | H | H | benzoyl |
| 40 | OH | Me | H | H | H | H | H | H | bromo |
| 41 | OH | Me | H | H | H | H | H | H | 3-Cl-4-F-phenyl |
| 42 | OCF2H | Me | H | H | H | H | H | H | phenyl |
| 43 | OH | Me | H | H | H | H | H | H | 5-(2-Et-pyridinyl) |
| 44 | OH | Me | H | H | H | H | 5-(2-Et-pyridinyl) | H | H |
| 45 | OH | Me | H | H | H | H | 4-CF3-phenyl | H | H |
| 46 | OH | Me | H | H | H | H | H | H | 4-CF3-phenyl |
| 47 | OH | Me | H | H | H | H | H | H | 4-tert-butylphenyl |
| 48 | OH | Me | H | H | H | H | H | H | 4-acetylphenyl |
| 49 | OH | Me | H | H | H | H | 4-acetylphenyl | H | H |
| 50 | OH | Me | H | H | H | H | H | H | 4-carboxyphenyl |
| 51 | OH | Me | H | H | H | H | H | H | 4-Et-phenyl |
| 52 | OH | Me | H | H | H | H | H | bromo | H |
| 53 | OMs | Me | H | H | H | H | H | H | phenyl |
| 54 | OH | Me | H | H | H | H | phenyl | H | H |
| 55 | OH | Me | H | H | H | H | 4-carboxyphenyl | H | H |
| 56 | OH | Me | H | H | H | H | 4-Cl-phenyl | H | H |
| 57 | OH | Me | H | H | H | H | 3-thienyl | H | H |
| 58 | OH | Me | H | H | H | H | 4-OCF3-phenyl | H | H |
| 59 | OH | Me | H | H | H | H | H | H | 3-thienyl |
| 60 | OH | Me | H | H | H | H | H | H | 2-thienyl |
| 61 | OH | Me | H | H | H | H | H | H | 2-naphthyl |
| 62 | OH | Me | H | H | H | H | H | H | 4-Cl-phenyl |
| 63 | OH | Me | H | H | H | H | H | H | 4-OCF3-phenyl |
| 64 | OH | Me | H | H | H | H | H | H | 2-benzothiophene |
| 65 | OH | Me | H | H | H | H | H | H | 4-F-phenyl |
| 66 | OH | Me | H | H | H | H | 2-F-phenyl | H | H |
| 67 | OH | Me | H | H | H | H | H | H | 4-Me-phenyl |
| 68 | OH | Me | H | H | H | H | H | H | 4-benzyloxyphenyl |

TABLE 1-continued

| Example | R¹ | R³ | R⁴ | R⁵ | R⁶ | R⁷ | R¹¹ | R¹² | R¹³ |
|---|---|---|---|---|---|---|---|---|---|
| 69 | OH | Me | H | H | H | H | H | H | α-OH-a-Me-benzyl |
| 70 | OH | Me | H | H | H | H | H | H | 1-naphthyl |
| 71 | OH | Me | H | H | H | H | H | H | 2-F-phenyl |
| 72 | OH | Me | H | H | H | H | H | H | 3-F-phenyl |
| 73 | OH | Me | H | H | H | H | H | H | 3-Cl-phenyl |
| 74 | OH | Me | H | H | H | H | H | 3-Cl-phenyl | H |
| 75 | OH | Me | H | H | H | H | H | 3-F-phenyl | H |
| 76 | OH | Me | H | H | H | H | H | H | 4-Cl-phenylsulfonyl |
| 77 | OH | Me | H | H | H | H | H | H | α-OH-a-Me-4-Cl-benzyl |
| 78 | OH | Me | H | H | H | H | H | H | 3-Cl-4-F-phenyl |
| 79 | OH | ethyl | H | H | H | H | H | H | 3-Cl-4-F-phenyl |
| 80 | OH | allyl | H | H | H | H | H | H | 3-Cl-4-F-phenyl |
| 81 | OH | n-propyl | H | H | H | H | H | H | 3-Cl-4-F-phenyl |
| 82 | OH | Me | H | H | H | H | H | H | 4-MeSO2 |
| 83 | OH | Me | H | H | H | H | H | 2-benzothiophene | H |
| 84 | OH | 4-Cl-benzyl | H | H | H | H | H | H | 3-Cl-4-F-phenyl |
| 85 | NH2 | Me | H | H | H | H | H | H | 3-Cl-4-F-phenyl |
| 86 | 2-(2-pyridinyl)ethoxy | Me | H | H | H | H | H | H | 3-Cl-4-F-phenyl |
| 87 | carbethoxymethoxy | Me | H | H | H | H | H | H | 3-Cl-4-F-phenyl |
| 88 | n-butoxy | Me | H | H | H | H | H | H | 3-Cl-4-F-phenyl |
| 89 | 2-(Methio)ethoxy | Me | H | H | H | H | H | H | 3-Cl-4-F-phenyl |
| 90 | O-(3,4-F-benzoyl) | Me | H | H | H | H | H | H | 3-Cl-4-F-phenyl |
| 91 | OAc | Me | H | H | H | H | H | H | 3-Cl-4-F-phenyl |
| 92 | Cl | Me | H | H | H | H | H | H | 3-Cl-4-F-phenyl |
| 93 | OCF2H | Me | H | H | H | H | H | H | phenylsulfonyl |
| 94 | OMs | Me | H | H | H | H | H | H | 3-Cl-4-F-phenyl |
| 95 | carboxymethoxy | Me | H | H | H | H | H | H | 3-Cl-4-F-phenyl |
| 96 | OCF2H | Me | H | H | H | H | H | H | bromo |
| 97 | OCF2H | Me | H | H | H | H | H | bromo | H |
| 98 | OH | Me | H | H | H | H | H | H | dimethylcarbinol |
| 99 | OCF2H | Me | H | H | H | H | H | H | 4-Me-phenyl |
| 100 | OCF2H | Me | H | H | H | H | H | H | 3-Me-phenyl |
| 101 | OCF2H | Me | H | H | H | H | H | 4-Me-phenyl | H |
| 102 | OCF2H | Me | H | H | H | H | H | 3-Me-phenyl | H |
| 103 | NH2 | Me | H | H | H | H | H | H | Me |
| 104 | OH | Me | H | H | H | H | H | CO2Et | H |
| 105 | OCF2H | allyl | H | H | H | H | H | H | 3-Cl-4-F-phenyl |
| 106 | OH | 2-Me-2-propene | H | H | H | H | H | H | 3-Cl-4-F-phenyl |
| 107 | OH | Me | H | H | H | H | H | dimethylcarbinol | H |
| 108 | OH | propargyl | H | H | H | H | H | H | 3-Cl-4-F-phenyl |
| 109 | OH | 2-bromo-2-propene | H | H | H | H | H | H | 3-Cl-4-F |
| 110 | OH | allyl | H | H | H | H | H | H | 4-Cl-thiophenoxy |
| 111 | OCF2H | allyl | H | H | H | H | H | H | 4-Cl-thiophenoxy |
| 112 | Me2N | Me | H | H | H | H | H | H | Me |
| 113 | NHAc | Me | H | H | H | H | H | H | Me |
| 114 | NH2 | allyl | H | H | H | H | H | H | 4-Cl-thiophenoxy |
| 115 | NHallyl | allyl | H | H | H | H | H | H | 4-Cl-thiophenoxy |
| 116 | NH2 | Me | H | H | H | H | H | H | bromo |
| 117 | 2-hydroxyethoxy | Me | H | H | H | H | H | H | 3-Cl-4-F-phenyl |
| 118 | NH2 | 2,2,2-trifluoroethyl | H | H | H | H | H | H | 3-Cl-4-F-phenyl |
| 119 | NH2 | Me | H | H | H | H | H | H | phenyl |
| 120 | NH2 | Me | H | H | H | H | H | H | 4-MeS-phenyl |
| 121 | NH2 | Me | H | H | H | H | H | H | 4-MeSO2-phenyl |
| 122 | NH2 | allyl | H | H | H | H | H | H | 3-Cl-4-F-phenyl |
| 123 | NH2 | allyl | H | H | H | H | H | H | 4-MeSO-phenyl |
| 124 | NH2 | allyl | H | H | H | H | H | H | 4-MeSO2-phenyl |
| 125 | NH2 | Me | H | H | H | H | H | H | 4-dimethylcarbinolphenyl |

Table 2 further illustrates compounds which are representative of the present invention.

TABLE 2

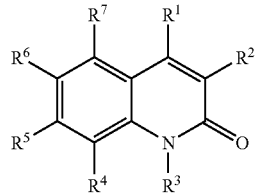

$R^4 = H; R^5 = H; R^6 = H; R^7 = H$

| Example | $R^1$ | $R^2$ | $R^3$ |
|---|---|---|---|
| 126 | OH | Me | benzyl |
| 127 | OH | n-butyl | benzyl |
| 128 | OH | tert-butyl | benzyl |
| 129 | OH | phenetyl | benzyl |
| 130 | OH | isobutyl | benzyl |
| 131 | OH | α-methylbenzyl | benzyl |
| 132 | OH | benzoyl | benzyl |
| 133 | OMe | benzoyl | benzyl |
| 134 | OH | α-hydroxybenzyl | benzyl |
| 135 | OH | cyclohexylmethyl | methyl |
| 136 | OH | naphthylmethyl | methyl |
| 137 | OH | n-heptyl | methyl |
| 138 | OH | n-butyl | methyl |
| 139 | OH | 3-phenyl-2-propenyl | methyl |
| 140 | OH | 3-phenyl-propyl | methyl |
| 141 | OH | phenethyl | methyl |
| 142 | OH | 1-naphthylmethyl | methyl |
| 143 | OH | 4-(4-Cl-thiophenoxy)benzoyl | methyl |
| 144 | NH2 | 2-(3-Cl-4-F-phenyl)-5-picolyl | methyl |

Table 3 further illustrates compounds which are representative of the present invention.

TABLE 3

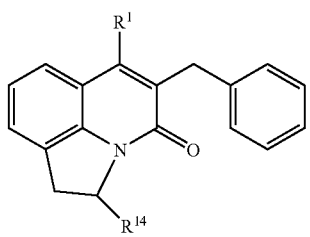

| Example | $R^1$ | $R^{14}$ |
|---|---|---|
| 9 | OH | H |
| 10 | OMe | H |
| 11 | OBn | H |
| 12 | OH | Methyl |
| 13 | OH | Phenyl |
| 14 | OMe | Phenyl |
| 15 | H | Phenyl |

The invention will now be illustrated in the following non-limiting Examples in which, unless otherwise stated:
1. All the end products of the Formula A and intermediates were analyzed by NMR and TLC;
2. Most compounds were purified by flash chromatography on silica gel, recrystallization and/or swish (stirring vigorously a suspension in a solvent followed by filtration of the solid); and
3. The course of reactions was followed by thin layer chromatography (TLC) and reaction times are given for illustration only.

General procedure:

Method A

To N-methyl-4-hydroxy-2-quinolone (0.5 g, 2.8 mmol) and an aldehyde (4.3 mmol) in toluene (20 mL) at 22° C. was added triethylsilane (1.4 mL, 8.8 mmol) and TFA (1.0 ml, 13 mmol). The reaction mixture was stirred at reflux for 3 h, cooled to 22° C. and poured into aqueous $NaHCO_3$ and extracted with EtOAc. The organic extract was washed ($H_2O$, brine), dried ($MgSO_4$), filtered and concentrated. Purification by flash chromatography or crystallization from hexane-EtOAc (or hexane-$Et_2O$) afforded the title compound.

Method B

Step 1

To a stirred solution of the acyl chloride (1.1 eq) in DCM (0.5 M) at room temperature was added anthranilonitrile (1 eq). After 15 minute, triethylamine (1.5 eq) was added and the mixture stirred overnight. The product is filtered off and the filtrate is diluted with ethyl acetate, extracted with water and a saturated solution of ammonium chloride. Purification was by flash chromatography or crystallization from hexane-EtOAc (or hexane-$Et_2O$).

Step 2

The compound from step 1 was suspended in ThF at room temperature and then treated with a solution of potassium tert-butoxide in THF (1 eq), stirred 20 minutes then methyl iodide (1 eq) was added, the progress of the alkylation is followed by TLC. When completed, the reaction was treated again with a solution of potassium tert-butoxide in THF (1 eq). After completion by TLC, the reaction mixture is diluted with ethyl acetate and water, washed with a saturated solution of ammonium chloride, a saturated solution of sodium chloride. Purification by flash chromatography or crystallization from hexane-EtOAc (or hexane-$Et_2O$) afforded the title compound.

EXAMPLE 13

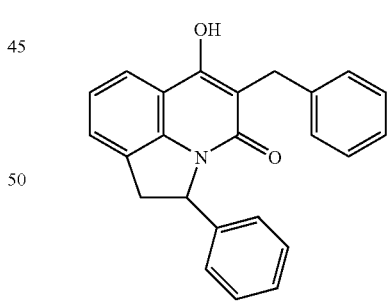

5-Benzyl-6-hydroxy-2-phenyl-1,2-dihydro-pyrrolo[3,2,1-ij]quinolin-4-one

2-Phenylindoline and diethylbenzyl malonate was heated to 140° C. over 1 h distilling off EtOH. The mixture was gradually heated up to 280° C. and maintained at this temperature for 2 h. Cooling afforded a solid which was stirred vigourously in hot ethyl acetate for 1 h. The desired compound was isolated after filtration as a beige solid. m.p. 252-254° C.

EXAMPLE 16

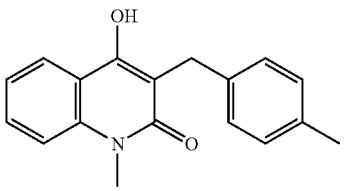

4-hydroxy-1-methyl-3-(4-methylbenzyl)quinolin-2(1H)-one

Following the procedures described in General Method A and using 4-methylbenzaldehyde, the title compound was isolated as white powder after purification by flash chromatography (hexane-ethyl acetate, 8:2). An alternative procedure is General Method B, replacing anthranilonitrile with methyl 2-aminobenzoate and 3-(4-methylphenyl)propanoyl chloride.

$^1$H NMR (400 MHz, acetone-$d_6$) δ 10.1 (s, OH), 8.09 (d, 1H), 7.56 (t, 1H), 7.54 (d, 1H), 7.22 (m, 3H), 7.0 (d, 2H), 4.0 (s, 2H), 3.6 (s, 3H), 2.03 (s, 3H).

EXAMPLE 38

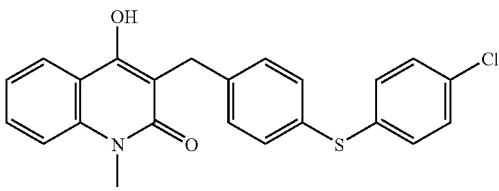

3-{4-[(4-chlorophenyl)thio]benzyl}-4-hydroxy-1-methylquinolin-2(1H)-one

Following the procedures described in General Method A and using 4-[(4-chlorophenyl)thio]benzaldehyde from example 114, step 1, the title compound was isolated as white powder after purification by flash chromatography (hexane-ethyl acetate, 3:2).

$^1$H NMR (400 MHz, DMSO-$d_6$): δ 10.5 (s, 1H), 8.02 (d, 1H), 7.62 (t, 1H), 7.48 (d, 1H), 7.36 (d, 2H), 7.29 (m, 5H), 7.17 (d, 2H), 3.98 (s, 2H), 3.58 (s, 3H).

EXAMPLE 110

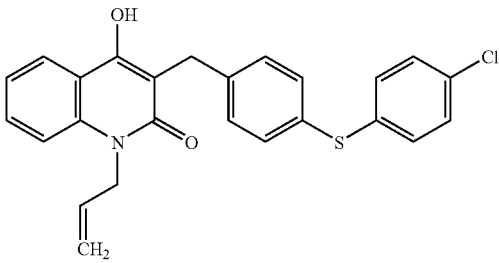

1-allyl-3-{4-[(4-chlorophenyl)thio]benzyl}-4-hydroxyquinolin-2(1H)-one

Following the procedures described in Example 114, replacing anthranilonitrile with methyl 2-aminobenzoate in step 1 of General Method B, the title compound was isolated as white powder after purification by flash chromatography (hexane-ethyl acetate, 8:2).

$^1$H NMR (400 MHz, acetone-$d_6$) δ 8.03 (d, 1H), 7.55 (t, 1H), 7.43-7.34 (m, 4H), 7.30-7.14 (m, 6H), 5.87 (m, 1H), 5.09 (d, 1H), 4.93-4.86 (m, 3H), 3.98 (d, 2H).

EXAMPLE 114

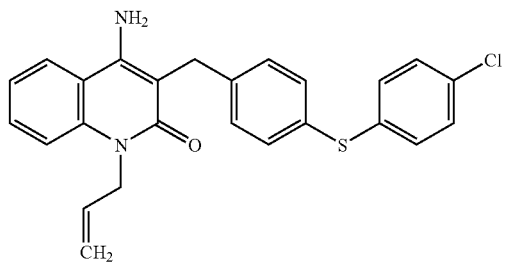

1-allyl-4-amino-3-{4-[(4-chlorophenyl)thio]benzyl}quinolin-2(1H)-one

Step 1: 4-[(4-chlorophenyl)thio]benzaldehyde

A solution of 4-fluoro-benzaldehyde (1 eq), 4-chloro-benzenethiol (1.0 eq) and sodium carbonate (1.5 eq) in DMF (0.16 M) was heated at 100° C. for 3 h then 18 h at rt. The mixture was diluted with ether and water, the organic phase washed with brine and the solvents evaporated. The residue was purified by stirring vigorously in hexane-ether followed by filtration to give the title compound as a white solid.

Step 2: methyl (2E)-3-{4-[(4-chlorophenyl)thio]phenyl}prop-2-enoate

A solution of aldehyde (1 eq) from step 1 and methyl triphenylphosphoranylidene acetate (1.4 eq) in toluene (0.3M) was heated at 100° C. for 4 h. After evaporation of the solvents, the residue was purified by flash chromatography (hexane-ethyl acetate, 9:1) to give the title compound as a white solid.

Step 3: methyl 3-{4-[(4-chlorophenyl)thio]phenyl}propanoate

A solution of ester from step 2 in EtOAc (0.2M) containing 10% Pd/C (0.15 g/mmol) was agitated under hydrogen (50 psi, Parr apparatus) for 3 h. The mixture was filtered over Celite and the solvent evaporated to afford the title compound.

Step 4: 3-{4[(4-chlorophenyl)thio]phenyl}propanoic acid

A solution of ester from step 3 and LiOH (2N, 3 eq) in MeOH (0.2M) was stirred at reflux for 2 h, cooled to rt and acidified to pH 3 with HCl 10%. The mixture was extracted with ether and the solvent evaporated. The residue was purified by stirring vigorously in hexane followed by filtration to give the title compound as a white solid.

Step 5: 3-{4-[(4-chlorophenyl)thio]phenyl}propanoyl chloride

To a solution of acid from step 4 in $CH_2Cl_2$ (0.2M) was added oxalyl chloride (1.2 eq) and one drop of DMF. The mixture was stirred at rt for 3 h and the solvent evaporated. The crude acid chloride was used as such in the next step.

Step 6: 1-allyl-4-amino-3-{4-[(4-chlorophenyl)thio]benzyl}quinolin-2(1H)-one

Following the procedures described in General Method B, using acid chloride from previous step 5 and replacing methyl iodide by allyl bromide in step 2 of General Method B, the title compound was isolated as white foam after purification by flash chromatography (hexane-ethyl acetate, 8:2).

$^1$H NMR (400 MHz, acetone-$d_6$) δ 7.95 (dd, 1H), 7.52 (dt, 1H), 7.39 (m, 3H), 7.30 (m, 4H), 7.20 (m, 3H), 5.98-5.92 (m, 1H), 5.81 (s, 2H), 5.12-5.0 (m, 2H), 4.97 (m, 2H), 4.07 (s, 2H).

EXAMPLE 145

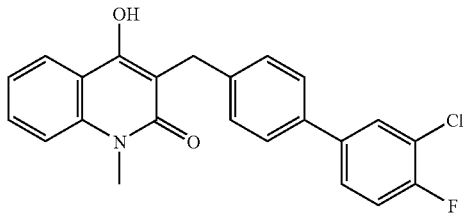

3-[(3'-chloro-4'-fluoro-1,1'-biphenyl-4-yl)methyl]-4-hydroxy-1-methylquinolin-2(1H)-one Following the procedures described in General Method A and using 4-[(3-chloro-4-fluorophenyl)]benzaldehyde, stirring vigorously the residue in acetone followed by filtration, the title compound was isolated as white powder.

EXAMPLE 146

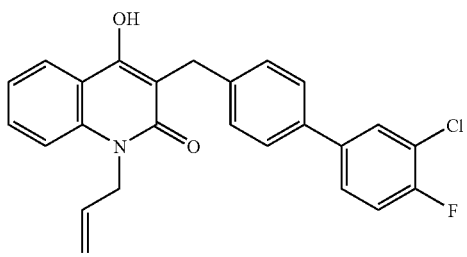

1-allyl-3-[(3'-chloro-4'-fluoro-1,1'-biphenyl-4-yl)methyl]4-hydroxyquinolin-2(1H)-one Following the procedures described in Example 110, the title compound was isolated as white powder after purification by flash chromatography (hexane-ethyl acetate, 8:2) and stirring vigorously the residue in ether followed by filtration.

$^1$H NMR (400 MHz, acetone-$d_6$) δ 10.6 (s, OH), 8.04 (d, 1H), 7.79 (dd, 1H), 7.61 (m, 1H), 7.54-7.31 (m, 7H), 7.23 (t, 1H), 5.88 (m, 1H), 5.09 (d, 1H), 4.92 (d, 1H), 4.87 (s, 2H), 4.02 (s, 2H).

EXAMPLE 147

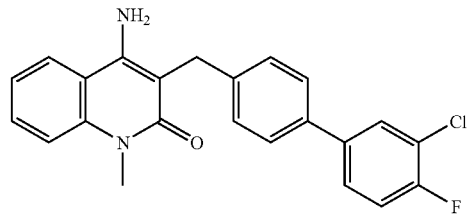

4-amino-3-[(3'-chloro-4'-fluoro-1,1'-biphenyl-4-yl)methyl]-1-methylquinolin-2(1H)-one Following the procedures described in Example 114, the title compound was isolated as white powder after purification by flash chromatography (hexane-ethyl acetate, 8:2) and stirring vigorously the residue in ether followed by filtration.

$^1$H NMR (300 MHz, CDCl$_3$): δ 7.58-7.49 (m, 3H), 7.41-7.24 (m, 6H), 7.21-7.11 (m, 2H), 4.45 (s, NH$_2$), 4.11 (s, 2H), 3.74 (s, 3H).

EXAMPLE 148

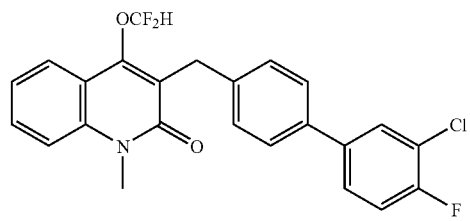

3-[(3'-chloro-4'-fluoro-1,1'-biphenyl-4-yl)methyl]-4-(difluoromethoxy)-1-methylquinolin-2(1H)-one A solution of example 145, Cs$_2$CO$_3$ (2 eq) in DMF (0.2M) was heated at 100° C. (open flask) then methyl chlorodifluoroacetate (2 eq) was added and the mixture stirred at 90-110° C. for 3 h. After cooling to rt, the mixture was diluted with water, extracted with ethyl acetate and the solvent evaporated. The residue was purified by crystallisation in hexane\ether to give the title compound as a white powder.

$^1$H NMR (400 MHz, acetone-$d_6$) δ 7.89 (d, 1H), 7.76-7.68 (m, 2H), 7.65-7.52 (m, 4H), 7.48-7.33 (m, 4H), 7.05 (t, 1H), 4.15 (s, 2H), 3.75 (s, 3H).

EXAMPLE 149

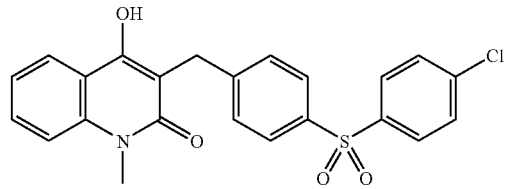

3-{4-[(4-chlorophenyl)sulfonyl]benzyl}-4-hydroxy-1-methylquinolin-2(1H)-one

Step 1: 4-[(4-chlorophenyl)sulfonyl]benzaldehyde

A solution of 4-[(4-chlorophenyl)thio]benzaldehyde from example 114, step1 and mCPBA (2.2 eq) in $CH_2Cl_2$ was stirred at rt for 1 h then $Ca(OH)_2$ (2.2 eq) was added. The mixture was stirred 30 min, filtered and the solvent evaporated. The residue was purified by stirring vigorously in hexane-ether followed by filtration to give the title compound as a white solid.

Step2: 3-{4-[(4-chlorophenyl)sulfonyl]benzyl}4-hydroxy-1-methylquinolin-2(1H)-one Following the procedures described in General Method A and using aldehyde from step 114, the title compound was isolated as white powder after purification by stirring vigorously in ethyl acetate-chloroform-ether followed by filtration.

$^1$H NMR (400 MHz, DMSO-$d_6$): δ 10.6 (s, 1H), 8.02 (d, 1H), 7.90 (d, 2H), 7.82 (d, 2H), 7.65 (d, 2H), 7.58 (dt, 1H), 7.44 (m, 3H), 7.25 (t, 1H), 4.03 (s, 2H), 3.54 (s, 3H).

ASSAYS FOR DETERMINING BIOLOGICAL ACTIVITY

The compound of Formula A can be tested using the following assays to determine their prostanoid antagonist or agonist activity in vitro and in vivo and their selectivity. The prostaglandin receptor activities demonstrated are DP, $EP_1$, $EP_2$, $EP_3$, $EP_4$, FP, IP and TP.

Stable Expression of Prostanoid Receptors in the Human Embryonic Kidney (HEK) 293(ebna) Cell Line Prostanoid receptor cDNAs corresponding to full length coding sequences are subcloned into the appropriate sites of mammalian expression vectors and transfected into HEK 293(ebna) cells. HEK 293(ebna) cells expressing the individual cDNAs are grown under selection and individual colonies are isolated after 2-3 weeks of growth using the cloning ring method and subsequently expanded into clonal cell lines.

Prostanoid Receptor Binding Assays

HEK 293(ebna) cells are maintained in culture, harvested and membranes are prepared by differential centrifugation, following lysis of the cells in the presence of protease inhibitors, for use in receptor binding assays. Prostanoid receptor binding assays are performed in 10 mM MES/KOH (pH 6.0) (EPs, FP and TP) or 10 mM HEPES/KOH (pH 7.4) (DP and IP), containing 1 mM EDTA, 10 mM divalent cation and the appropriate radioligand. The reaction is initiated by addition of membrane protein. Ligands are added in dimethylsulfoxide which is kept constant at 1% (v/v) in all incubations. Non-specific binding is determined in the presence of 1 µM of the corresponding non-radioactive prostanoid. Incubations are conducted for 60 min at room temperature or 30° C. and terminated by rapid filtration. Specific binding is calculated by subtracting non specific binding from total binding. The residual specific binding at each ligand concentration is calculated and expressed as a function of ligand concentration in order to construct sigmoidal concentration-response curves for determination of ligand affinity.

Prostanoid Receptor Agonist and Antagonist Assays

Whole cell second messenger assays measuring stimulation ($EP_2EP_4$, DP and IP in HEK 293(ebna) cells) or inhibition ($EP_3$ in human erythroleukemia (HEL) cells) of intracellular cAMP accumulation or mobilization of intracellular calcium ($EP_1$, FP and TP in HEK 293(ebna) cells stably transfected with apo-aequorin) are performed to determine whether receptor ligands are agonists or antagonists. For cAMP assays, cells are harvested and resuspended in HBSS containing 25 mM HEPES, pH 7.4. Incubations contain 100 µM RO-20174 (phosphodiesterase type IV inhibitor, available from Biomol) and, in the case of the $EP_3$ inhibition assay only, 15 µM forskolin to stimulate cAMP production. Samples are incubated at 37° C. for 10 min, the reaction is terminated and cAMP levels are then measured. For calcium mobilization assays, cells are charged with the co-factors reduced glutathione and coelenterazine, harvested and resuspended in Ham's F12 medium. Calcium mobilization is measured by monitoring luminescence provoked by calcium binding to the intracellular photoprotein aequorin. Ligands are added in dimethylsulfoxide which is kept constant at 1% (v/v) in all incubations. For agonists, second messenger responses are expressed as a function of ligand concentration and both $EC_{50}$ values and the maximum response as compared to a prostanoid standard are calculated. For antagonists, the ability of a ligand to inhibit an agonist response is determined by Schild analysis and both $K_B$ and slope values are calculated.

Rat Paw Edema Assay

The method is the same as described in Chan et al (J. Pharmacol. Exp. Ther. 274: 1531-1537, 1995).

LPS-Induced Pyrexia in Conscious Rats

The method is the same as described in Chan et al (J. Pharmacol. Exp. Ther. 274: 1531-1537, 1995).

LPS-Induced Pyrexia in Conscious Squirrel Monkeys

The method is the same as described in Chan et al (Eur. J. Pharmacol. 327: 221-225, 1997).

Acute Inflammatory Hyperalgesia Induced by Carrageenan in Rats

The method is the same as described in Boyce et al (Neuropharmacology 33: 1609-1611, 1994).

Adjuvant-Induced Arthritis in Rats

Female Lewis rats (body weight ~146-170 g) are weighed, ear marked, and assigned to groups (a negative control group in which arthritis was not induced, a vehicle control group, a positive control group administered indomethacin at a total daily dose of 1 mg/kg and four groups administered with a test compound at total daily doses of 0.10-3.0 mg/kg) such that the body weights were equivalent within each group. Six groups of 10 rats each were injected into a hind paw with 0.5 mg of *Mycobacterium butyricum* in 0.1 mL of light mineral oil (adjuvant), and a negative control group of 10 rats was not injected with adjuvant. Body weights, contralateral paw volumes (determined by mercury displacement plethysmography) and lateral radiographs (obtained under Ketamine and Xylazine anesthesia) were determined before (day-1) and 21 days following adjuvant injection, and primary paw volumes were determined before (day-1) and on days 4 and 21 following adjuvant injection. The rats were anesthetized with an intramuscular injection of 0.03-0.1 mL of a combination of Ketamine (87 mg/kg) and Xylazine (13 mg/kg) for radiographs and injection of adjuvant. The radiographs were made of both hind paws on day 0 and day 21 using the Faxitron (45 kVp, 30 seconds) and Kodak X-OMAT TL film, and were developed in an automatic processor. Radiographs were evaluated for changes in the soft and hard tissues by an investigator who was blinded to experimental treatment. The following radiographic changes were graded numerically according to severity: increased soft issue volume (0-4), narrowing or widening of joint spaces (0-5) subchondral erosion (0-3), periosteal reaction (0-4), osteolysis (0-4) subluxation (0-3), and degenerative joint changes (0-3). Specific criteria were used to establish the numerical grade of severity for each radiographic change. The maximum possible score per foot was 26. A test compound at total daily doses of 0.1, 0.3, 1and 3 mg/tg/day, indomethacin at a total daily dose of 1 mg/kg/day, or vehicle (0.5% methocel in sterile water) were administered per os b.i.d. beginning post injection of adjuvant and continuing for 21 days. The compounds are prepared weekly, refrigerated in the dark until used, and vortex mixed immediately prior to administration.

What is claimed is:

1. A compound of Formula B

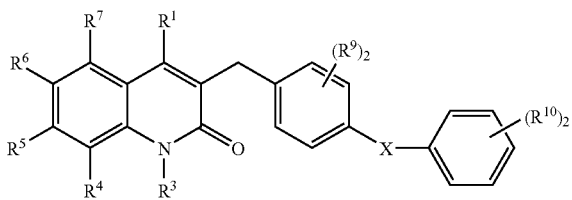

or a pharmaceutically acceptable salt, hydrate, ester or tautomer thereof, wherein:

X is selected from a bond, O or S(O)k, wherein k is 0, 1 or 2, $R^1$ is selected from the group consisting of:
(1) hydrogen,
(2) halo,
(3) hydroxy,
(4) $C_{1-6}$alkyl,
(5) $C_{1-6}$alkenyl,
(6) $C_{1-6}$alkoxy,
(7) $C_{1-6}$alkyl-S(O)$_m$—, wherein m is 0, 1, 2 or 3
(8) $C_{1-6}$alkyl-C(O)—
(7) $C_{1-6}$alkoxy-C(O)—
(9) $C_{1-6}$alkyl-C(O)—O—
(10) aryl,
(11) aralkyl,
(12) aryloxy,
(13) aralkoxy,
(14) arylthio,
(15) aroyl,
(16) aroyloxy and wherein the alkyl, alkenyl and aryl portions of items (4)-(16) above are optionally substituted from one up to the maximum number of substituable positions with a member independently selected from the group consisting of: halo, heterocycle, $C_{1-6}$alkoxy, $C_{1-6}$alkyl-S(O)$_k$—, $C_{1-6}$alkyl-C(O)—, $C_{1-6}$alkoxy-C(O), $C_{1-6}$alkyl-C(O)—O, carboxy, hydroxy and aralkoxy, the alkyl portions of said $C_{1-6}$alkoxy, $C_{1-6}$alkyl-S(O)$_k$—, $C_{1-6}$alkyl-C(O)—, $C_{1-6}$alkoxy-C(O) and $C_{1-6}$alkyl-C(O)—O groups optionally substituted with 1-3 substituents independently selected from: halo and hydroxy, said aryl portions of items (10)-(16) above further optionally substituted from one up to the maximum number of substituable positions with $C_{1-6}$alkyl, optionally substituted with 1-3 substituents independently selected from the group consisting of: halo and hydroxy;

$R^3$ is selected from the group consisting of:
(1) $C_{1-6}$alkyl, $C_{2-6}$alkenyl or $C_{3-6}$alkynyl, each optionally substituted with 1-3 halo groups.
(2) aryl, optionally substituted with 1-3 halo groups,
(3) aralkyl, optionally substituted with a substituent independently selected from the group consisting of: $C_{1-6}$alkylsulfonyl and halo, $R^4$, $R^5$, $R^6$ and $R^7$ are each independently selected from the group consisting of:
(1) hydrogen,
(2) halo, and
(3) $C_{1-6}$alkyl, optionally substituted with 1-3 halo groups, $R^8$ is selected from the group consisting of H, $C_{1-6}$alkyl, $C_{1-6}$alkenyl, $C_{1-6}$alkyl-C(O)—and aryl, the aryl, alkyl and alkenyl portions are optionally substituted with 1-3 halo groups, $R^9$ and $R^{10}$ are independently selected from the group consisting of:
(1) halo,
(2) $C_{1-6}$alkyl,
(3) $C_{1-6}$alkenyl,
(4) $C_{1-6}$alkoxy,
(5) $C_{1-6}$alkyl-S(O)$_k$—, wherein k is 0, 1 or 2,
(6) $C_{1-6}$alkyl-C(O)—,
(7) $C_{1-6}$alkoxy-C(O),
(8) $C_{1-6}$alkyl-C(O)—O—,
(9) carboxy,
(10) hydroxy, and
(11) N(R8)2, wherein the alkyl and alkenyl portions of items (2)-(8) above are optionally substituted from one up to the maximum number of substituable positions with a member independently selected from the group consisting of: halo, heterocycle, $C_{1-6}$alkoxy, $C_{1-6}$alkyl-S(O)$_k$—, $C_{1-6}$alkyl-C(O)—, $C_{1-6}$alkoxy-C(O)—, $C_{1-6}$alkyl-C(O)—O—, aralkoxy, carboxy and hydroxy, the alkyl portions of said $C_{1-6}$alkoxy, $C_{1-6}$alkyl-S(O)$_k$—, $C_{1-6}$alkyl-C(O)—, $C_{1-6}$alkoxy-C(O) and $C_{1-6}$alkyl-C(O)—O groups optionally substituted with 1-3 substituents independently selected from halo and hydroxy.

2. The compound according to claim 1 wherein:

X is selected from a bond, O or S(O)k, wherein k is 0, 1 or 2, $R^1$ is selected from the group consisting of:
(1) halo,
(2) hydroxy,
(3) $C_{1-6}$alkyl,
(4) $C_{1-6}$alkoxy, and
(5) N($R^8$)$_2$, wherein $R^8$ is H or $C_{1-4}$alkyl, wherein the alkyl portions of items (3)-(4) above are optionally substituted with 1-3 halo groups, $R^3$ is $C_{1-6}$alkyl or $C_{2-4}$alkenyl, each optionally substituted with 1-3 halo groups.

$R^4$, $R^5$, $R^6$, $R^7$ and $R^9$ are each H, and $R^{10}$ is H or halo.

3. The compound according to claim 2 selected from the group consisting of:
(1) 3-{4-[(4-chlorophenyl)thio]benzyl}-4-hydroxy-1-methylquinolin-2(1H)-one;
(2) 1-allyl-3-{4-[(4-chlorophenyl)thio]benzyl}-4-hydroxyquinolin-2(1H)-one;

(3) 1-allyl-4-amino-3-{4-[(4-chlorophenyl)thio]benzyl}quinolin-2(1H)-one;

(4) 3-[(3'-chloro-4'-fluoro-1,1'-biphenyl-4-yl)methyl]-4-hydroxy-1-methylquinolin-2(1H)-one;

(5) 1-allyl-3-[(3'-chloro-4'-fluoro-1,1'-biphenyl-4-yl)methyl]-4-hydroxyquinolin-2(1H)-one;

(6) 4-amino-3-[(3'-chloro-4'-fluoro-1,1'-biphenyl-4-yl)methyl]-1-methylquinolin-2(1H)-one;

(7) 3-[(3'-chloro-4'-fluoro-1,1'-biphenyl-4-yl)methyl]-4-(difluoromethoxy)-1-methylquinolin-2(1H)-one; and (8) 3-{4-[(4-chlorophenyl)sulfonyl]benzyl}-4-hydroxy-1-methylquinolin-2(1H)-one.

4. 4-amino-3-[(3'-chloro-4'-fluoro-1,1'-biphenyl-4-yl)methyl]-1-methylquinolin-2(1H)-one; or a pharmaceutically acceptable salt thereof.

5. A pharmaceutical composition comprising the compound of claim 1 and a pharmaceutically acceptable carrier.

6. A pharmaceutical composition comprising the compound of claim 4 and a pharmaceutically acceptable carrier.

* * * * *